United States Patent [19]

Misch

[11] Patent Number: 5,501,598
[45] Date of Patent: Mar. 26, 1996

[54] DENTAL TOOTH SYSTEM

[76] Inventor: Carl E. Misch, 410 Claremount, Dearborn, Mich. 48124

[21] Appl. No.: 98,524

[22] Filed: Jul. 28, 1993

[51] Int. Cl.$^6$ .............................. A61C 13/08; A61C 13/10
[52] U.S. Cl. ............................................ 433/197; 433/192
[58] Field of Search ................................. 433/191, 192, 433/197, 201.1, 202.1

[56] References Cited

U.S. PATENT DOCUMENTS

| | | | |
|---|---|---|---|
| 1,665,357 | 4/1928 | Gysi | 433/197 |
| 2,072,127 | 3/1937 | Pilkington et al. | 433/197 |
| 2,932,893 | 4/1960 | Marder | 433/192 |
| 3,252,220 | 5/1966 | Goddard | 433/197 |
| 3,305,926 | 2/1967 | Gerber | 433/197 |
| 3,316,639 | 5/1967 | Shovers | 433/197 |
| 3,947,963 | 4/1976 | Haker | 433/197 |
| 4,194,288 | 3/1980 | Hass | 433/197 |
| 4,795,345 | 1/1989 | Ai et al. | 433/192 X |

Primary Examiner—Nicholas D. Lucchesi
Attorney, Agent, or Firm—Brooks & Kushman

[57] ABSTRACT

A denture tooth system (10) for a partially or completely edentulous patient, comprising a block of denture teeth (12), each tooth including enlarged undercut surfaces (14) disposed thereupon to permit greater mechanical retention to a rigid base to which the block (12) is secured. The denture tooth system (10) also includes a reduced gingival contour (16) to accommodate implanted attachments or bars and one or more teeth opposing the block. Each one or more posterior opposing teeth includes an enlarged central fossa (20). The block (12) is positioned and configured so that only a lingual cusp (22) of a given maxillary posterior tooth occludes with the central fossa (20) of one of the one or more opposing mandibular posterior teeth in centric occlusion.

20 Claims, 2 Drawing Sheets

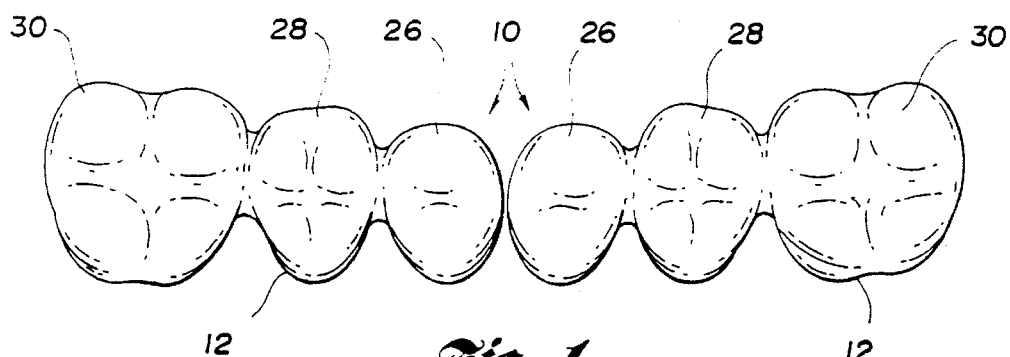
Fig. 1
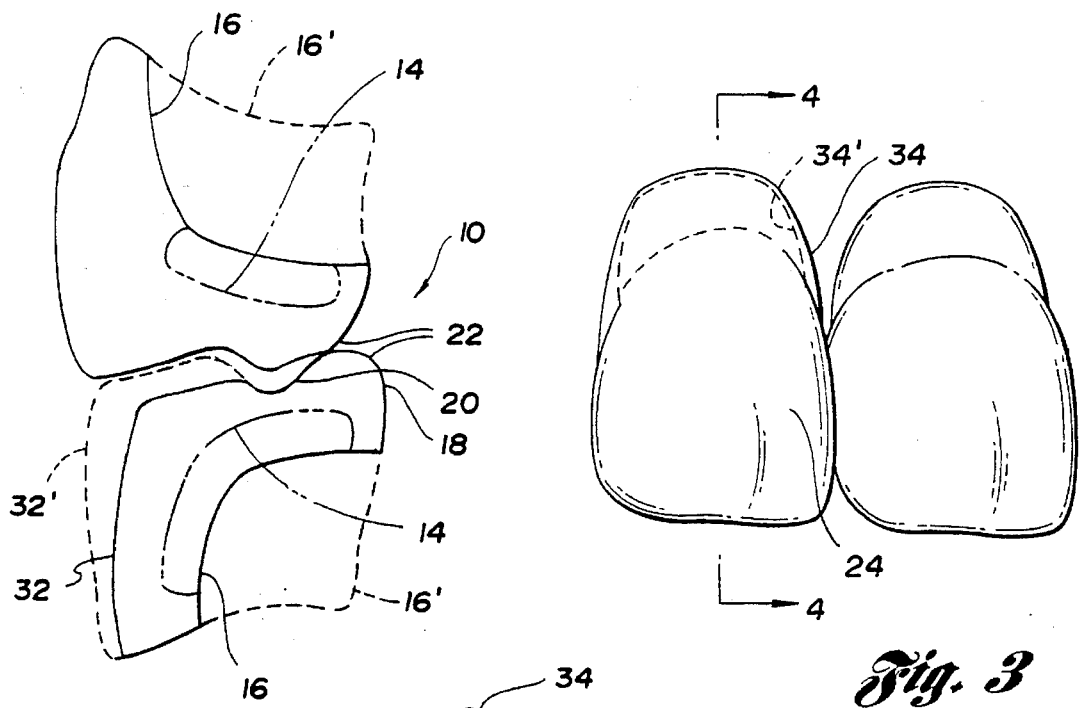
Fig. 2
Fig. 3
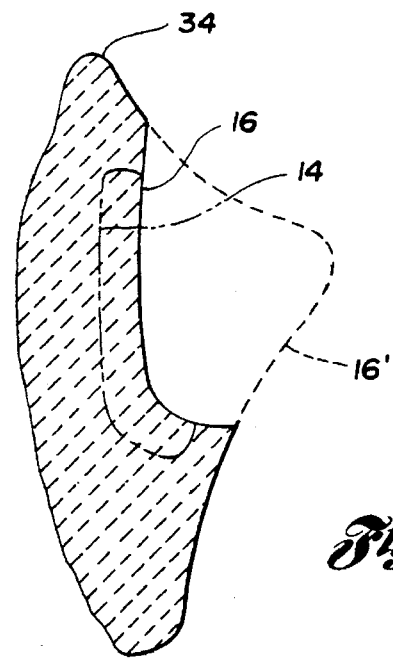
Fig. 4

DENTAL TOOTH SYSTEM

BACKGROUND

1. Field of the Invention

This invention relates to a denture tooth system for use in implant dentistry (artificial tooth roots) and prosthodontics (restoration of crowns, partial dentures or dentures), and particularly to the design and insertion of oral structures to restore the loss of contour, comfort, function, aesthetics, speech, and health to the partially or completely edentulous patient. More specifically, the invention discloses denture teeth for a maxillary and/or mandibular denture opposing an implant-supported overdenture, fixed prosthesis, or natural dentition.

2. Summary of Related Art

The arrangement of denture is defined in the Glossary of Prosthodontic Terms (1968) as "the placement of teeth on a denture or temporary base with definite objectives in mind." It includes the establishment of the plane of occlusion (where the teeth are in reference to a horizontal plane) and the occlusal scheme (how the teeth come together).

A pre-fabricated denture tooth concept has been known for more than 70 years. The ability to place a pre-made denture tooth, held by wax, and attached to a denture base has been used by dentists for decades. Many types of pre-made denture teeth are available. Such teeth are most often produced as individual units, e.g. central incisor, lateral incisor, canine, first premolar, second premolar, first molar, and second molar for the maxillary (upper) teeth and mandibular (lower) teeth.

Lack of stability and lack of retention are the most common complications related to removable prostheses. The mandibular denture has more associated problems than an opposing maxillary prosthesis. Patients often feel that retention and stability of maxillary dentures is acceptable. As a result, a common treatment plan for an edentulous patient uses implants to support the mandibular restoration and a traditional soft tissue-supported maxillary denture.

Postinsertion complications of the removable maxillary restoration may be anticipated. The patient may complain of maxillary denture sore spots and instability of the restoration. The causes for the complications are related to the implant supporting a mandibular prosthesis, which provide improved forces, function, proprioception (awareness of a structure in time and place), and stability. The sore spots under the maxillary denture result because patients with rigid fixated oral implant prostheses are able to generate masticatory forces approaching that of natural teeth, while complete denture wearers have been shown to exert only 25% of such forces.

Maxillary denture instability is related to increased patient awareness and the conditions of a more stable mandibular prosthesis. A conventional soft-tissue-borne complete removable mandibular prosthesis moves to accommodate prematurities or inaccuracy of occlusion. Occlusal position is often anterior to the recorded centric relation occlusion. In addition, the patient is accustomed to the mandibular denture lifting up in the posterior when the mandible goes into excursions, and no posterior teeth are in contact. In contrast, with a rigid mandibular restoration, the maxillary prosthesis moves to accommodate the mandibular occlusion so the occlusal concepts must be more accurate. This predisposes to maxillary denture instability, soreness, mucosal changes, and ultimately to resorption of the ridge. The maxillary prosthesis will even lose the valve seal retention and be dislodged when the mandibular implant restoration proceeds into excursive movements without posterior contact. This not only occurs with the incision of food, but also during parafunction (repeated or sustained occlusion). Inadequate valve seal and instability of the maxillary denture can also contribute to gagging.

Mandibular implant overdentures provide greater proprioception. Also, the mandible occludes in a more consistent centric relation occlusion position than would a traditional denture. The occlusal forces are directed in a more consistent direction and location. This requires a more exact occlusal scheme and registration. In many ways, the combination of a complete maxillary denture against a lower mandible implant-supported prosthesis resembles a single complete maxillary denture opposing mandibular natural dentition.

The occlusal surfaces of the dental arches do not conform to a flat plane. A plane of occlusion has three aspects: occluso-gingival, anterior-posterior, and bucco-lingual. The occluso-gingival direction is established by the anterior incisal edge. The bucco-lingual (horizontal) dimension is parallel with a line drawn through the pupils of the eyes. The anterior-posterior (vertical) dimension establishes the height of the posterior occlusal plane.

Once the anterior lip position and incisal edge location are initially determined, the posterior maxillary plane of occlusion is designed. It is often determined in the laboratory from the canine incisal edge position to a point halfway up the retromolar pad. The end result is an occlusal plane below the natural teeth position. In principle, this improves the stability of a lower denture. The lowered plane of occlusion helps decrease moment forces on the lower denture, and the tongue rest position is above the posterior teeth. But when the mandibular restoration is implant supported, the same technique is not indicated, as it places the posterior maxillary teeth lower than the original natural tooth position and makes the maxillary denture more unstable.

Camper's plane connects the lower border of the alar process of the nose to the middle or most distal portions of the tragus of the ear. The occlusal plane has been reported to be parallel to this reference plane.

The maxillary edentulous posterior ridge resorbs in a medial direction as it transforms from abundant bone to severe atrophy bony support. Therefore, the maxillary denture tooth gradually becomes more cantilevered off the bone support, even when positioned in the same spatial location. The mandibular edentulous posterior ridge also resorbs in a medial direction as it transforms from abundant bone to moderate bone, but then resorbs laterally from a moderate bone division, and more laterally as it resorbs to severe atrophy.

In posterior tooth positioning for complete dentures, the position of the mandibular posterior tooth is often first determined. Bone support concepts of occlusion often position the mandibular teeth perpendicular to the edentulous ridge. This positions the central fossae of the posterior mandibular teeth more medial than that of their natural predecessors in cases of minimum bone loss, but more facial in moderate to advanced and very facial in severe bone loss, compared to the natural tooth placement. Mandibular dentures in the "neutral zone" record the tongue position and also result with posterior teeth more buccal in resorbed arches than the natural tooth placement. This in turn results in the maxillary teeth being placed farther facial in the moderate to severe bone loss patient, if a normal cusp-fossa relation is maintained. Consequently, maxillary denture teeth are always placed lateral to the resorbing bony support. The condition is compounded when the resorption of the bone is moderate to severe and the mandibular teeth are positioned over bony support or neutral muscular zones.

The maxillary posterior tooth is also involved in aesthetics, especially the premolar region. The more lateral tooth placement affects aesthetics when compared with the position of the natural teeth.

The basic concepts of lingualized occlusion were first suggested by S. H. Payne, Dent. Dig. 47:20–22 (1941). E. Pound discussed a similar concept and introduced the term "lingualized" occlusion. J. Prosthet. Dent. 24:586–600 (1970)). Pound placed the lingual cusp of the mandibular posterior teeth between lines drawn from the canine to each side of the retromolar pad. The buccal maxillary cusps were ground off by Payne, while the buccal cusps of the mandibular teeth were removed by Pound. Consistent in their philosophy was the belief that the lingual cusp was the only area of maxillary tooth contact. These occlusal schemes were designed to narrow the occlusal table and improve mastication, reduce forces to the underlying bone, and help stabilize a lower denture. The techniques of Payne and Pound may be modified further to a medial positioned lingualized occlusion, as disclosed herein.

Tooth "pop-off" or loss from a denture is an embarrassment for the patient and problem for doctor-patient relations. This may occur as a result of force or contamination of the bonding surface. The denture tooth may be contaminated from the custom recontouring process for fit over a bar or attachment. As a result, the tooth bond to the denture may be contaminated or reduced in size, thus increasing the risk of tooth loss.

Additional information about the related art appears in "Contemporary Implant Dentistry," C. E. Misch (1993), Chapter 13 entitled "Maxillary Denture Opposing an Implant Overdenture or Fixed Prosthesis," of which is incorporated here by reference.

Against this background, there remains a need for a dental tooth system which will provide occlusal rehabilitation for the completely or partially edentulous implant patient. Such a system would disclose specific tooth designs for reduced fabrication time, maximum retention in the denture base, and minimal adjustments in occlusal contact, while presenting an aesthetic appearance.

SUMMARY OF THE INVENTION

The present invention discloses a dental tooth system for a partially or completely edentulous patient. The system includes a block of denture teeth which are curved so as to follow contours which correspond to mandubular movements. In the block, each tooth has an enlarged undercut surface to permit greater mechanical retention to a rigid base to which the block is secured. Each tooth also has a reduced gingival contour to accommodate implanted attachments or bars.

The posterior block of teeth include the first and second premolars and a first molar. The second molars are independent.

The block is positioned and configured so that only a lingual cusp of a given maxillary posterior tooth occludes with the central fossa of mandibular posterior teeth when in centric occlusion.

In one embodiment, the block also includes the maxillary and mandibular central incisors (left and right).

The dental tooth system also discloses a plane analyzer having a radius of 3⅞" to 4⅛" and a thickness of 2 mm to help in waxing opposing metal work and allowing 2 mm for porcelain. This permits the block of denture teeth or individual denture teeth to be set.

Additionally, the disclosed dental tooth system includes a wax spatula with a radius of curvature of 3⅞" to 4⅛" for adjusting wax rims with compensating curves.

BRIEF DESCRIPTION OF THE DRAWINGS

FIG. 1 depicts a top plan view of two denture blocks, each having three posterior teeth (first and second premolars and first molar) incorporating an arch-form curvature, according to the present invention;

FIG. 2 depicts a side elevational view of posterior teeth, illustrating a reduced lingual gingival contour, an enlarged undercut, and a reduced buccal cusp, together with an enlarged central fossa;

FIG. 3 illustrates a front view of anterior teeth having a greater cervical contour in relation to a normal tooth;

FIG. 4 is a cross sectional view of the tooth depicted in FIG. 3 taken along the line 4—4 thereof showing a reduced gingival contour and enlarged area for mechanical retention;

DETAILED DESCRIPTION OF THE PREFERRED EMBODIMENTS

Figure 5:
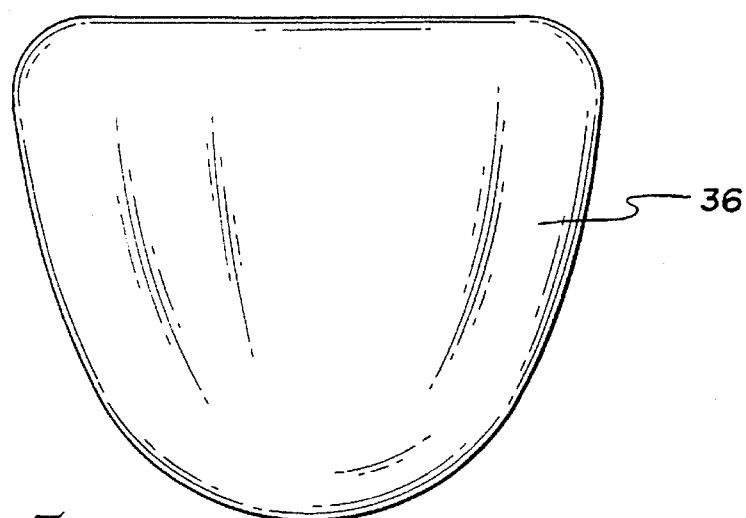
FIG. 5 is an occlusal plane analyzer.

Turning now to FIGS. 1–4 of the drawings, there is depicted a dental tooth system 10 for a partially or completely edentulous patient. The system 10 comprises a block 12 of denture teeth. Each tooth in the block 12 includes an enlarged undercut surface 14 (FIGS. 2 and 4) disposed thereupon to permit greater mechanical retention to a rigid base (not shown) to which the block 12 is secured. Each tooth also has a reduced gingival contour 16 to accommodate implanted attachments or bars. The contour 16 is shown in relation to contour 16' which depicts a typical contour exhibited by prior art structures.

Opposing the block 12 are one or more teeth 18 (FIG. 2), each of which include an enlarged central fossa 20.

The block 12 is positioned and configured so that only a maxillary lingual cusp 22 of a given tooth occludes with mandibular central fossa 20 of one of the one or more opposing teeth in centric occlusion.

A first aspect of the present invention addresses the posterior portion of the mouth. The present inventor has evaluated the existing occlusal plane from the canine to first molar in 50 patients with natural maxillary teeth. In 50% of the patients, the parallel posterior reference point on the tragus was in the upper third, in 46% it was parallel to the mid tragus, and 4% it was below this reference on the right side of the patient's head. The position was different on the contralateral side in almost 25% of the patients. Therefore, it can be suggested that the posterior plane of occlusion with natural teeth is either parallel to or above Camper's line.

When a maxillary denture is fabricated, the maxillary wax rim is made parallel to Camper's plane for upper arches with good bone and with good retentive form. The posterior reference point is raised to a position near the upper third of the tragus, slightly raising the occlusal plane, to make the maxillary denture more stable for patients with more bone loss. Thus the anterior occlusal plane is correlated to the length and support of the maxillary lip; ridge shape, height, and position; phonetics, and aesthetics. The posterior occlusal plane corresponds to the amount of bone, the retentive form of the arch, and to a plane from the middle to the upper portion of the tragus of the ear to the inferior portion of the ala of the nose.

If the posterior occlusal plane is too high, the maxillary denture base can be driven forward on the tissues during the mandibular arc of closure. In addition, the posterior plane of occlusion may compromise the action of the tongue when placing food on the occlusal table. The ideal plane of occlusion for a denture opposing an implant denture is similar to that found with the natural teeth, and most often corresponds to the mid to upper third of the tragus.

Once the posterior occlusion is established in relation to the ala of the nose and tragus, the buccalingual plane is determined. The anterior plane is usually parallel to the pupils of the eyes. However, on rare occasion the eyes are not parallel to the horizontal plane and a reevaluation is required.

The vertical occlusal dimension is then established with a mandibular base plate and wax rim. The superstructure bar for an implant supported prosthesis over anterior root forms is not fabricated until the actual tooth position has been established. On the other hand, a mandibular subperiosteal restoration already has the superstructure in place at this time, and the baseplate and wax rim may be firmly attached to the bar. This permits a very stable and rigid recording of the vertical occlusal dimension.

The inventor observed 30 patients with natural mandibular posterior teeth and compared the lingual cusp position to the position stated by Pound. In all patients, the position of the posterior lingual tooth extended medial to a line drawn from the canine to the medial aspect of the retromolar pad. In the majority of patients, the lingual cusps extended 2 mm beyond the line, while in approximately 10% they extended to 3 mm, and in another third, were 1 mm beyond the line. Therefore, denture teeth set more medial to the retromolar pad are more similar in position to natural teeth than the region established by Pound. The tooth position suggested by Pound helps stabilize a mandibular denture. An implant-supported overdenture does not require tooth position as the primary stability factor. In addition, the more medial the posterior denture teeth, the more vertical are the occlusal forces over the maxillary bone. This reduces tipping forces and makes the upper denture more stable during occlusal contacts.

The position of the posterior line is drawn from the mandibular canine to the lingual side of the retromolar pad. The mandibular posterior teeth are placed so that the central fossa is over this line and the lingual aspect of the tooth extends medial to the line. The greater the maxillary posterior resorption, the more medial the lingual cusps. However, the lingual aspect of the mandibular teeth does not extend beyond 3 mm of a line drawn from the lingual aspect of the retro molar pad to the canine tooth. This positions the denture tooth more medial than previous techniques, yet the lingual aspect of the denture tooth is still in a similar location to that of the natural tooth.

The occlusal centric contacts follow the guidelines of lingualized occlusion from Payne and Pound. Only the lingual cusps of the maxillary posterior teeth are in contact during centric occlusion (FIG. 2). A maxillary denture occlusion cannot separate the left and right component, or the anterior and posterior influence. Because all teeth are joined to a rigid baseplate, the occlusal contacts in one region affect the entire restoration. A tripod occlusion to stabilize a tooth, or anterior contact to prevent overeruption of teeth, is not required.

Because the primary contact is the lingual cusp of the maxillary teeth rather than the buccal cusp of the mandibular teeth, an additional stabilizing factor for the maxillary denture teeth relative to the underlying bone is evidenced. In addition, a narrower occlusal table is observed, which decreases the force required to penetrate food and simplifies the occlusal adjustment process. The maxillary posterior teeth are positioned more medial than past techniques, as they follow the more medial positioned mandibular teeth. The more medial position of the maxillary buccal cusp also permits the polished labial surface of the denture to slope from the vestibule toward the occlusal surface, so the buccinator muscle may help improve denture base retention.

Bilateral balance is suggested to improve denture stability during parafunction. Once food is introduced between the teeth, the balanced occlusion is of less benefit for stability. Payne and Pound did not suggest a bilateral balance occlusion. However, since the lower implant denture is more stable than its maxillary counterpart, the maxillary denture may rotate and become dislodged during parafunction. This causes additional stress on the premaxilla and may result in more anterior resorption. Constant dislodgement of the posterior seal may also cause additional gagging in the patient. Therefore, the stable mandibular denture warrants additional stability of the maxillary prosthesis. It is more important to balance the occlusion within the functional range of mandibular movement, rather than to the extremes of lateral border positions.

The occlusal and incisal surfaces of all crowns taken together in either arch do not contact a flat plane. Looking at the teeth from a point opposite the first molar buccally, one sees that a line following the occlusal and incisal surfaces describes a curve called the curve of Spee. The composite arrangement of the occlusal surfaces of all of the teeth in each dental arch approximately conforms to a segment of a sphere which gives the curvature a 3-dimensional quality. This curvature is called the compensating occlusal curvature. The compensating occlusal curvature of the mandibular teeth is concave, that of the maxillary teeth is convex. When the two arches are brought together in centric occlusion, these curved planes become identical.

A compensating curve may be used in the posterior occlusion. An occlusal analyzer follows the contours of a 3⅞" to 4⅛" radius sphere. Thus, the curved outer surface of a segment of a sphere may have a radius which varies considerably in different individuals. Posterior block teeth which follow this sphere permit the technician to follow the occlusal plane. Prior art block teeth are not set to a compensating curve, and therefore do not permit bilateral balanced occlusion.

Figure 6:
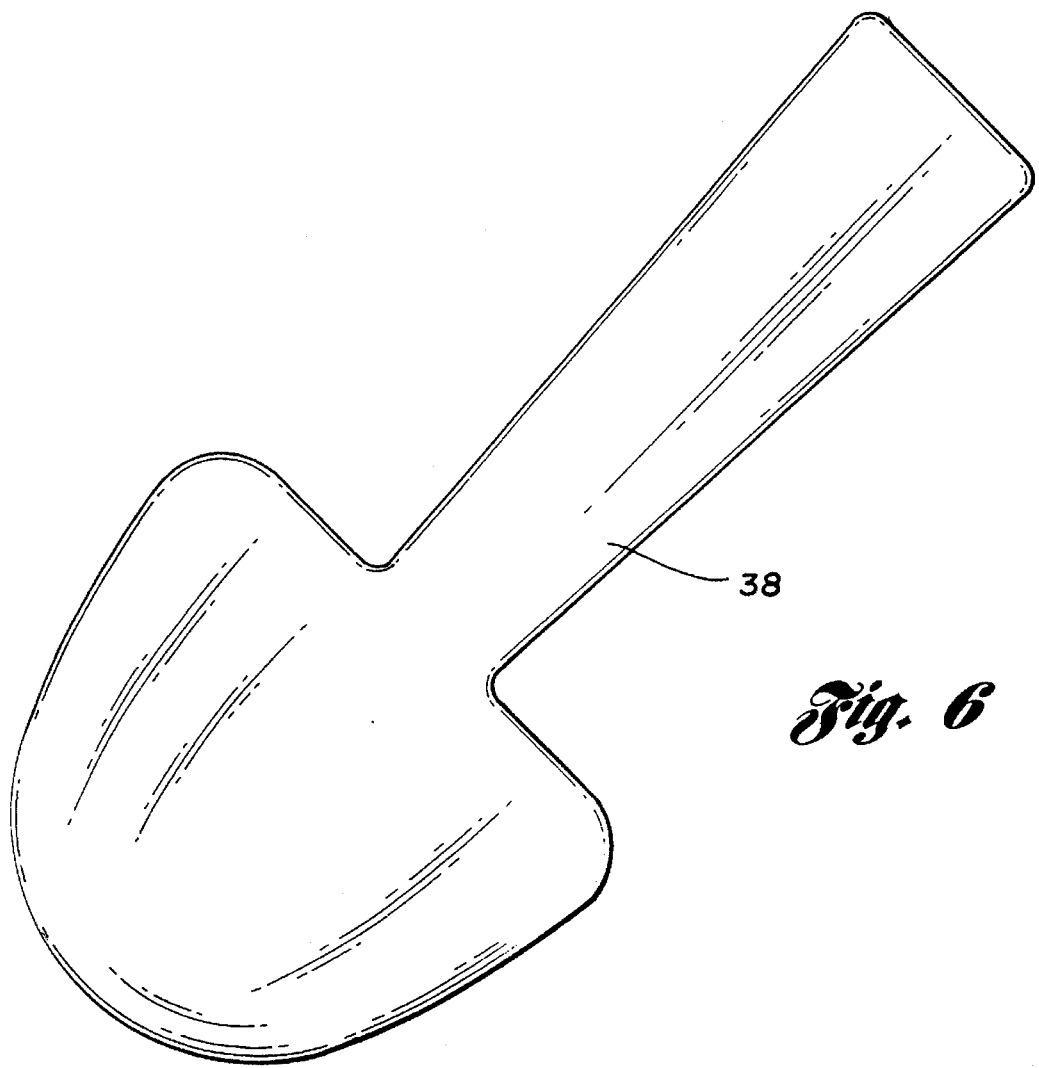
FIG. 6 is a wax spatula.

The dental tooth system of the present invention also includes a plane analyzer (FIG. 5) having a radius of 3⅞" to 4⅛" and a thickness of about 2 mm. The plane analyzer essentially follows the ideal compensating curve in waxing opposing metal work, while allowing about 2 mm for porcelain, thereby permitting the block of denture or individual teeth to be set following the compensating curve. To adjust wax rims with compensating curves, the disclosed dental tooth system also includes a wax spatula (FIG. 6) having a radius of curvature 3⅞" to 4⅛". Prior art wax spatulas are flat, with no reference to any compensating plane.

A moment force or torque is applied during occlusion to the maxillary teeth set facial to the residual ridge, and becomes greater as the crown height is increased. This condition is difficult to prevent in the anterior maxilla, because this position is required for proper aesthetics and phonetics. However, setting the teeth and the occlusal contacts in the posterior region toward the midline and raising the posterior plane of occlusion reduces moment forces and associated instability. The maxillary second molar may even be set in cross-bite to further improve the vertical force component over the severe atrophic posterior maxilla.

The resultant factors of raising the posterior occlusal plane, "medial position" of the teeth, "lingual occlusion," and bilateral balance help stabilize the weakest member of the removable protheses, the maxillary denture.

In summary, the following sequence governs the implanted posterior tooth position:

1. Position the block of mandibular teeth. The central fossae are placed over the line from the medial retromolar pad to the canine. The greater the resorption of posterior maxilla, the more medial the mandibular lingual cusp location (the lingual tooth position does not extend beyond 3 mm lingual of the retromolar pad to the canine cusp tip line).

2. Position the block of maxillary posterior buccal cusp so only lingual cusps occlude with mandibular central fossa in centric relation occlusion. The maxillary second molar may be set in cross-bite for patients with severe atrophy, and is independent of the posterior block of teeth.

3. Bilateral balance occlusion in limited mandibular excursions is established by the built-in compensating curve of the posterior teeth.

The invention discloses teeth which are more stable, have better function, and are easier to place. Also, there is less tooth debonding or loss, and faster fabrication of removable or fixed prostheses requiring pre-made replacement teeth.

Thus, the present invention discloses a block denture tooth which improves the current state of the art by offering a denture tooth and arrangement specific for mandibular dentures that have implant support or maxillary dentures or implant overdentures opposing natural teeth or mandibular overdentures.

In the present invention, the maxillary posterior block teeth are provided as a 3 tooth block 12 (first premolar 26, second premolar 28, and first molar 30). The maxillary teeth are very similar in form to current full anatomic teeth. However, they are designed as a block for more rapid assembly during fabrication, and correspond to a 3⅞" to 4⅛" radius sphere for a compensating curve. This curvature also permits a balanced occlusion. Previous block teeth set ups are flat, and do not permit balanced occlusion (e.g. Shovers, et al. U.S. Pat. No. 3,316,639).

Mandibular posterior block teeth are also provided as one 3 tooth block (first premolar 26, second premolar 28, and first molar 30). The teeth are designed with a wider central fossa 20 (FIG. 2), lower buccal cusps 32, as compared to that of the prior art 32', and a reduced buccal cusp contour. Accordingly, only the maxillary lingual cusp occludes with the central fossa of the lower teeth in centric occlusion (jaw centered in the joint when closing). The lingual cusp 22 is higher than the buccal cusp 32 to prevent tongue biting and to keep the food on the occlusal table.

A separate second molar tooth is available, but not included in the block, since this tooth position is more flexible and should be customized to each patient's condition.

An additional feature of the disclosed invention is to reduce laboratory time in setting teeth over bars or attachments, and decreasing the risk of denture tooth pop-off or loss during function. The buccal gingival region is longer than natural teeth for greater mechanical retention. The lingual contour is less than 4 mm for easier placement over the implant components. Overdentures often require the undersurface of the denture tooth to be modified to accommodate attachments or bars. The facial and occlusal (incisal) parts of the tooth are not modified, but the remaining portion is grossly removed. (FIGS. 2 and 4.) Since the teeth have less dimension on the lingual and under surface, they do not require custom recontouring to fit over a bar or attachment. Therefore, the laboratory phase is faster and easier.

Patients with implant supported overdentures generate greater forces than denture wearers, and tooth loss or "pop-off" can also occur from this extra force. Accordingly, the tooth block 12 of the present invention has a significant hollow and undercut region 14 (FIG. 2), along with a longer buccal gingival contour 16. The denture base acrylic is incorporated into this enlarged area. Acrylic receives its strength by bulk. Present undercuts are too small to have sufficient strength to prevent fracture of the small acrylic zone. In addition, since the teeth are in a larger block compared to single teeth, there is better mechanical retention.

Movement of the teeth often occurs during the denture processing from wax to acrylic. The maxillary and mandibular block tooth 12 is better able to resist processing forces, and movement is less likely. This reduces correction after processing. A great deal of time is spent by the lab technician in making marginal ridges level, the central fossa in a straight line and the proper anterior-posterior curve. The block tooth of the present invention eliminates the time and detail for these steps.

After the mandibular posterior teeth are set in wax, the maxillary teeth must be set so that occlusion is proper, the marginal ridges even, and the lingual cusps straight. The disclosed block tooth allows this step to be one process rather than 9 steps (3 for each of 3 teeth).

The adjacent anterior teeth on juxtaposed 3-teeth blocks on the same arch have their central incisors joined together. Since these teeth have a constant position relative to each other, they are set in an ovoid arch form and fused at the mesial contact region. This allows rapid placement and more ability to remove the lingual contour for placement over a bar. The block tooth is also less likely to be lost, since more bulk of material is present for denture base incorporation. The lateral and canine teeth also have significant undercuts and lingual contour reduction (FIG. 4).

Patients often have periodontal disease before they lose their teeth. The teeth appear longer in the anterior for a significant length of time before tooth loss. Many patients ask for a longer tooth, yet present teeth are designed with a restricted cervical and often darker color (just like a natural tooth). Yet, these patients perceive that their teeth should be longer, wider at the neck and the same color. The disclosed anterior maxillary tooth has a longer labial portion (FIG. 4). The normal cervical line is present, but above this line the tooth is the same contour and color as the non-cervical parts thereof. The longer facial contour also provides greater retention to the base plate.

The present invention also discloses a tooth system which has a wax spatula 36 (FIG. 5) and template set on a 3⅞"–4⅛" sphere. Conventional wax rims have been on a monoplane. A curvature on a wax spatula 38 (FIG. 6) allows a curvature on the wax rim. This allows a better representation for the wax rim used to determine the occlusal plane.

The 3⅞"–4⅛" template allows the dentist/technician to help set the block teeth once the vertical dimension is determined.

Accordingly, the disclosed tooth system (teeth, spatula, template) has the following advantages:

I. The block tooth system has aesthetic looking maxillary teeth set on a natural tooth-like compensating curve.

II. The lingual cusp design of the disclosed block tooth system allows the upper denture to be more stabilized with unilateral forces. The lingual occlusion directs the force to where the bone is on the maxilla.

III. Block teeth are faster to set, move less in processing, and pop-off or are lost less often. The hollow design and reduced lingual contour of the disclosed invention provides room for implant bars or attachments.

Having above indicated a preferred embodiment of the present invention, it will occur to those skilled in the art that modifications and alternatives can be practiced within the spirit of the invention. It is accordingly intended to define the scope of the invention only as indicated in the following claims.

What is claimed is:

1. A dental tooth system for a partially or completely edentulous patient, comprising:
   a block of denture teeth in which individual teeth are interconnected for stability and secured to a rigid base, each tooth including
   enlarged undercut surfaces disposed buccal and lingual on the medial and lateral aspects thereof to permit greater mechanical retention to the rigid base to which the block is secured, and
   a reduced gingival contour to accommodate implanted attachments or bars, thereby allowing the block of denture teeth to be positioned medially;
   denture teeth opposing the block, each of the opposing teeth including an enlarged central fossa,
   the block being positioned and configured so that only a lingual cusp of a given tooth of said block occludes with the central fossa of an opposing tooth in centric occlusion, wherein
   occlusal surfaces of the denture teeth opposing the block of teeth and teeth in the block are configured so that they lie on imaginary spheres, thereby allowing a balanced occlusion while forming a medial positioned lingual occlusion.

2. The dental tooth system of claim 1, wherein
   the block of denture teeth comprises a maxillary posterior block of teeth.

3. The dental tooth system of claim 2, wherein the maxillary posterior block includes:
   artificial first premolar, second premolar, and first molar teeth, said denture teeth opposing the block comprising a reduced buccal cusp and an enlarged central fossa.

4. The dental tooth system of claim 3, wherein
   each lingual cusp of mandibular teeth is higher than its associated buccal cusp to prevent biting of the tongue and to keep food on an occlusal table.

5. The dental tooth system of claim 2, wherein
   the central fossae of teeth in the block of denture teeth are aligned over a line extending from a mandibular canine to a lingual side of a retromolar pad.

6. The dental tooth system of claim 5, wherein
   a lingual aspect of the denture teeth opposing the block lie within 3 mm of the line, so that a lingual aspect of teeth in the block of denture teeth corresponds closer to a maxillary bone loss position.

7. The dental tooth system of claim 6, wherein
   occlusal surfaces of the denture teeth opposing the maxillary block of teeth are configured so that they lie on an imaginary sphere having a radius in the range of 3⅞" to 4⅛", thereby allowing a balanced occlusion while forming a medial positioned lingual occlusion.

8. The dental tooth system of claim 1, wherein
   the block of denture teeth comprises a maxillary posterior block and said denture teeth opposing the block comprise an implant prosthesis.

9. The dental tooth system of claim 1, wherein
   the block of denture teeth comprises a mandibular posterior block.

10. The dental tooth system of claim 1, wherein
    the block of denture teeth comprises a mandibular posterior block and said denture teeth opposing the block comprise an implant prosthesis.

11. The dental tooth system of claim 1, wherein
    the block of denture teeth comprises a maxillary posterior block and said denture teeth opposing the block comprise a mandibular posterior block.

12. The dental tooth system of claim 1, wherein
    the block of denture teeth comprises a maxillary anterior block.

13. The dental tooth system of claim 12, wherein the maxillary anterior block of denture teeth comprises a block of two teeth.

14. The dental tooth system of claim 13, wherein teeth in the maxillary anterior block have a wider cervical contour of a similar color to non-cervical parts of the teeth in the maxillary anterior block.

15. The dental tooth system of claim 1, wherein
    the block of denture teeth comprises a mandibular anterior block.

16. The dental tooth system of claim 15, wherein the mandibular anterior block of denture teeth comprises a block of two teeth.

17. The dental tooth system of claim 1, further including:
    a second molar tooth for use with the block.

18. The dental tooth system of claim 1, also including a plane analyzer having a radius of 3⅞" to 4⅛" and a thickness of 2 mm to help in waxing opposing metal work, and allowing 2 mm for porcelain, while permitting the block or individual denture teeth to be set along natural contours.

19. The dental tooth system of claim 1, also including a wax spatula having a curvature radius of 3⅞" to 4⅛" for adjusting wax rims with compensating curves.

20. A dental tooth system for a partially or completely edentulous patient, comprising:
    a block of denture teeth secured to a rigid base, each tooth including
    enlarged undercut surfaces disposed on the buccal and lingual medial and lateral aspects thereof to permit greater mechanical retention to the rigid base to which the block is secured, and
    a reduced gingival contour to accommodate implanted attachments or bars;
    denture teeth opposing the block, each of the teeth including an enlarged central fossa,
    the block being positioned and configured so that only a maxillary lingual cusp of a given tooth occludes with a central fossa of an opposing mandibular tooth in centric occlusion, the occlusal surfaces of each opposing mandibular tooth lying on an imaginary sphere.

* * * * *